US008067602B2

(12) United States Patent
Shao (10) Patent No.: US 8,067,602 B2
(45) Date of Patent: Nov. 29, 2011

(54) ASYMMETRIC CYANINE FLUORESCENT DYES, COMPOSITIONS AND THEIR USE IN STAINING BIOLOGICAL SAMPLES

(75) Inventor: Jianhui Shao, Nanshan (CN)

(73) Assignee: Shenzhen Mindray Bio-Medical Electronics Co., Ltd., Shenzhen (CN)

(*) Notice: Subject to any disclaimer, the term of this patent is extended or adjusted under 35 U.S.C. 154(b) by 452 days.

(21) Appl. No.: 12/334,274

(22) Filed: Dec. 12, 2008

(65) Prior Publication Data

US 2009/0176270 A1    Jul. 9, 2009

(30) Foreign Application Priority Data

Jan. 4, 2008 (CN) .......................... 2008 1 0002503

(51) Int. Cl.
| | |
|---|---|
| A01N 1/02 | (2006.01) |
| C12Q 1/68 | (2006.01) |
| G01N 33/53 | (2006.01) |
| G01N 33/00 | (2006.01) |
| G01N 33/48 | (2006.01) |
| C07D 215/18 | (2006.01) |
| C07D 215/04 | (2006.01) |
| C07D 419/00 | (2006.01) |
| C07D 417/00 | (2006.01) |
| C07D 413/00 | (2006.01) |
| C07D 401/00 | (2006.01) |
| C07D 409/00 | (2006.01) |
| C07D 411/00 | (2006.01) |
| C07D 405/00 | (2006.01) |
| C07D 213/00 | (2006.01) |

(52) U.S. Cl. ............ 546/165; 435/2; 435/6.1; 435/7.1; 436/91; 436/63; 436/800; 546/180; 546/181; 546/268.4; 546/270.1; 546/271.7; 546/277.4; 546/281.1; 546/284.1; 546/339

(58) Field of Classification Search .................. 548/120, 548/121; 436/91, 800; 435/6, 7.1, 7.2; 546/152
See application file for complete search history.

(56) References Cited

U.S. PATENT DOCUMENTS

| | | | |
|---|---|---|---|
| 3,883,247 A | 5/1975 | Adams | |
| 3,883,274 A | 5/1975 | Vuaille | |
| 4,122,348 A | 10/1978 | Bruck | |
| 4,146,604 A | 3/1979 | Kleinerman | |
| 4,286,963 A | 9/1981 | Ledis et al. | |
| 4,325,706 A | 4/1982 | Gershman et al. | |
| 4,332,785 A | 6/1982 | Allen et al. | |
| 4,336,029 A | 6/1982 | Natale | |
| 4,386,146 A * | 5/1983 | Kishino et al. .................. 430/95 |
| 4,414,325 A | 11/1983 | Masuda et al. | |
| 4,447,547 A | 5/1984 | Allen et al. | |
| 4,485,175 A | 11/1984 | Ledis et al. | |
| 4,528,274 A | 7/1985 | Carter et al. | |
| 4,529,705 A | 7/1985 | Larsen | |
| 4,544,546 A | 10/1985 | Wang et al. | |
| 4,571,388 A | 2/1986 | O'Connell et al. | |
| 4,596,035 A | 6/1986 | Gershman et al. | |
| 4,617,275 A | 10/1986 | Matsuda et al. | |
| 4,637,986 A | 1/1987 | Brown et al. | |
| 4,707,451 A | 11/1987 | Sage et al. | |
| 4,745,071 A | 5/1988 | Lapicola et al. | |
| 4,751,179 A | 6/1988 | Ledis et al. | |
| 4,822,745 A | 4/1989 | Burns et al. | |
| 4,882,284 A | 11/1989 | Kirchanski et al. | |
| 4,883,867 A | 11/1989 | Lee et al. | |
| 4,933,293 A | 6/1990 | Kuroda et al. | |
| 4,957,870 A | 9/1990 | Lee et al. | |
| 4,971,917 A | 11/1990 | Kuroda | |
| 4,978,624 A | 12/1990 | Cremins et al. | |
| 4,981,803 A | 1/1991 | Kuroda | |

(Continued)

FOREIGN PATENT DOCUMENTS

CN    1101980    4/1995

(Continued)

OTHER PUBLICATIONS

Netzel, T., Nafisi, K., Zhao, M., Lenhard, J., Johnson, I., Base-Content Dependence of Emission Enhancements, Quantum Yields, and Lifetimes for Cyanine Dyes Bound to Double Strand DNA: Photophysical Properties of Monomeric and Bichromophoric DNA Stains, 1995, J. Phys. Chem., 99, 17936-17947.*

Kristine M. Sovenyhazy et al., 'Spectroscopic Studies of the Multiple Binding Modes of a Trimethine-Bridged Cyanine Dye with DNA'. Necleic Acids Research, 2003, vol. 31 No. 10, pp. 2561-2569.

L.G.S. Brooker et al., 'Color and constitution, VIII. Absorption of Unsymmetrical Carbocyanines'. Journal of the American Chemical Society, 1945, pp. 1889-1893.

(Continued)

*Primary Examiner* — Rita Desai
*Assistant Examiner* — Ben S Michelson
(74) *Attorney, Agent, or Firm* — Kory D. Christensen; Matthew S. Bethards; Stoel Rives LLP (57) ABSTRACT

Asymmetric cyanine fluorescent dyes are represented by general formula I. These kinds of dyes may be used as a staining agent for nucleic acids, with the spectra at 600-900 nm in the near-infrared region and without interference from background fluorescence. These kinds of dyes may be useful with small-type red semiconductor lasers as the light source (such as 633 nm). Compositions comprising these dyes and methods for staining biological samples using these dyes or compositions are also provided.

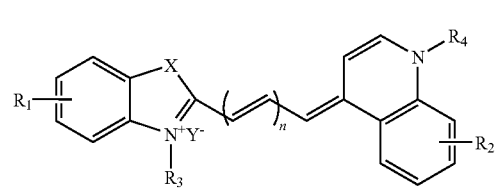

15 Claims, 6 Drawing Sheets

U.S. PATENT DOCUMENTS

| | | | |
|---|---|---|---|
| 4,985,174 A | 1/1991 | Kuroda et al. |
| 5,039,613 A | 8/1991 | Matsuda et al. |
| 5,075,556 A | 12/1991 | Fan et al. |
| 5,116,539 A | 5/1992 | Hamaguchi et al. |
| 5,155,044 A | 10/1992 | Ledis et al. |
| 5,175,109 A | 12/1992 | Sakata et al. |
| 5,179,026 A | 1/1993 | Matsuda et al. |
| 5,180,677 A | 1/1993 | Di Ianni et al. |
| 5,188,935 A | 2/1993 | Leif et al. |
| 5,227,304 A | 7/1993 | Wong |
| 5,232,857 A | 8/1993 | Lefevre et al. |
| 5,242,832 A | 9/1993 | Sakata |
| 5,250,437 A | 10/1993 | Toda et al. |
| 5,264,369 A | 11/1993 | Sakata et al. |
| 5,284,771 A | 2/1994 | Fan et al. |
| 5,316,725 A | 5/1994 | Carver et al. |
| 5,316,951 A | 5/1994 | Carver et al. |
| 5,321,130 A | 6/1994 | Yue et al. |
| 5,350,695 A | 9/1994 | Colella et al. |
| 5,360,739 A | 11/1994 | Fan et al. |
| 5,389,549 A | 2/1995 | Hamaguchi et al. |
| 5,411,891 A | 5/1995 | Fan et al. |
| 5,413,938 A | 5/1995 | Tsujino et al. |
| 5,438,003 A | 8/1995 | Colella et al. |
| 5,486,477 A | 1/1996 | Carver et al. |
| 5,492,833 A | 2/1996 | Rodriguez et al. |
| 5,496,734 A | 3/1996 | Sakata et al. |
| 5,510,267 A | 4/1996 | Marshall |
| 5,516,695 A | 5/1996 | Kim et al. |
| 5,518,928 A | 5/1996 | Cremins et al. |
| 5,538,893 A | 7/1996 | Sakata et al. |
| 5,559,037 A | 9/1996 | Kim et al. |
| 5,563,070 A | 10/1996 | Yamamoto et al. |
| 5,616,501 A | 4/1997 | Rodriguez et al. |
| 5,618,733 A | 4/1997 | Sakata et al. |
| 5,633,167 A | 5/1997 | Fan et al. |
| 5,639,630 A | 6/1997 | Malin et al. |
| 5,639,666 A | 6/1997 | Shenkin et al. |
| 5,656,449 A | 8/1997 | Yue |
| 5,677,183 A | 10/1997 | Takarada et al. |
| 5,686,308 A | 11/1997 | Li et al. |
| 5,691,204 A | 11/1997 | Kim et al. |
| 5,731,206 A | 3/1998 | Ledis et al. |
| 5,733,784 A | 3/1998 | Studholme et al. |
| 5,747,343 A | 5/1998 | Tsuchiya et al. |
| 5,763,280 A | 6/1998 | Li et al. |
| 5,773,299 A | 6/1998 | Kim et al. |
| 5,786,224 A | 7/1998 | Li et al. |
| 5,817,518 A | 10/1998 | Li et al. |
| 5,821,127 A | 10/1998 | Akai et al. |
| 5,821,128 A | 10/1998 | Provost |
| 5,840,515 A | 11/1998 | Provost |
| 5,843,608 A | 12/1998 | Li et al. |
| 5,858,667 A | 1/1999 | Dertinger et al. |
| 5,874,311 A | 2/1999 | Li et al. |
| 5,879,900 A | 3/1999 | Kim et al. |
| 5,882,934 A | 3/1999 | Li et al. |
| 5,891,731 A | 4/1999 | Akai et al. |
| 5,928,949 A | 7/1999 | Sakata et al. |
| 5,958,776 A | 9/1999 | Sakata et al. |
| 5,968,832 A | 10/1999 | Uchihashi et al. |
| 5,994,089 A | 11/1999 | Siiman et al. |
| 5,994,138 A | 11/1999 | Veriac |
| 6,004,816 A | 12/1999 | Mizukami et al. |
| 6,060,322 A | 5/2000 | Horton et al. |
| 6,100,038 A | 8/2000 | Dertinger et al. |
| 6,114,130 A | 9/2000 | Veriac et al. |
| 6,114,173 A | 9/2000 | Zelmanovic et al. |
| 6,197,593 B1 | 3/2001 | Deka et al. |
| 6,245,499 B1 | 6/2001 | Suzuki et al. |
| 6,271,035 B1 | 8/2001 | Deka et al. |
| 6,287,791 B1 | 9/2001 | Terstappen et al. |
| 6,350,613 B1 | 2/2002 | Wardlaw et al. |
| 6,368,864 B1 | 4/2002 | Deka et al. |
| 6,495,692 B1 | 12/2002 | Wang et al. |
| 6,524,858 B1 | 2/2003 | Zelmanovic et al. |
| 6,551,831 B2 | 4/2003 | Gupta et al. |
| RE38,131 E | 6/2003 | Uchihashi et al. |
| 6,630,990 B2 | 10/2003 | van't Dever et al. |
| 6,632,676 B1 | 10/2003 | Crews et al. |
| 6,664,110 B1 | 12/2003 | Tsuji et al. |
| 6,794,152 B2 | 9/2004 | Ryan et al. |
| 6,869,798 B2 | 3/2005 | Crews et al. |
| 6,900,023 B1 | 5/2005 | Houwen et al. |
| 6,955,872 B2 | 10/2005 | Maples et al. |
| 6,977,156 B2 | 12/2005 | Ryan et al. |
| 7,083,982 B2 | 8/2006 | Wang et al. |
| 7,235,404 B2 | 6/2007 | Lang et al. |
| 7,247,484 B2 | 7/2007 | Wu et al. |
| 7,300,797 B2 | 11/2007 | van Agthoven et al. |
| 7,405,082 B2 | 7/2008 | Mizukami et al. |
| 7,449,337 B2 | 11/2008 | Deka et al. |
| 7,465,584 B2 | 12/2008 | Matsumoto et al. |
| 2002/0182623 A1 | 12/2002 | Lefevre et al. |
| 2003/0145394 A1 | 8/2003 | Wang et al. |
| 2004/0241769 A1 | 12/2004 | Crews et al. |
| 2005/0202400 A1 | 9/2005 | Tsuji et al. |
| 2005/0272026 A1 | 12/2005 | Oguni |
| 2006/0177347 A1 | 8/2006 | Larsen et al. |
| 2007/0111276 A1 | 5/2007 | Lefevre et al. |
| 2007/0178597 A1 | 8/2007 | Tsuji et al. |
| 2008/0026475 A1 | 1/2008 | van Agthoven et al. |
| 2008/0131898 A1 | 6/2008 | Tsuji et al. |
| 2008/0176274 A1 | 7/2008 | Tsuji et al. |
| 2009/0023129 A1 | 1/2009 | Xu et al. |
| 2009/0176270 A1 | 7/2009 | Shao |
| 2010/0151509 A1 | 6/2010 | Ting et al. |
| 2010/0178654 A1 | 7/2010 | Kataoka et al. |

FOREIGN PATENT DOCUMENTS

| | | |
|---|---|---|
| CN | 1101982 | 4/1995 |
| CN | 1183559 | 6/1998 |
| CN | 1202621 | 12/1998 |
| CN | 1149397 | 5/2004 |
| EP | 0548983 | 6/1993 |
| EP | 0794435 | 9/1997 |
| WO | WO03104771 | 12/2003 |
| WO | WO9717471 | 5/2004 |

OTHER PUBLICATIONS

Jason A. Bordelon et al., 'Viscometry and Atomic Force Microscopy Studies of the Interactions of a Dimeric Cyanini Dye With DNA', J. Phys. Chem. B 2002, 106, 4838-4843.

Alexandre Furstenberg et al., 'Ultrafast Excited-State Dynamics of DNA Fluorescent Intercalators: New Insight Into the Fluorescence Enhancement Mechamisn,' J. Am. Chem. Soc. 2006, 128, 7661-7669.

U.S. Appl. No. 11/967,991, Xiaojun Peng et al.

Notice of Allowance in U.S. Appl. No. 11/967,897 dated Feb. 9, 2011.

Notice of Allowance dated Feb. 22, 2010 for U.S. Appl. No. 12/482,335.

Stephen J. Mason et al., 'Solid-Phase Catch, Activate, and Release Synthesis of Cyanine Dyes.' American Chemical Society Organic Letters, 2002, vol. 4 No. 24, pp. 4261-4264.

U.S. Appl. No. 12/482,335, filed Jun. 10, 2009, Saho Jianhui.

Stephen J. Mason et al., "Solid-Phase Catch, Activate, and Release Synthesis of Cyanine Dyes", American Chemical Society Organic Letters 2002, vol. 4 No. 24, pp. 4261-4264.

Notice of Allowance in U.S. Appl. No. 11/967,991 dated Aug. 7, 2009.

U.S. Appl. No. 12/843,671, filed Jul. 26, 2010, Zhao et al.

Notice of Allowance dated Aug. 7, 2009 for U.S. Appl. No. 11/967,991.

U.S. Appl. No. 12/580,474, filed Oct. 16, 2009, Yuji.

Notice of Allowance in U.S. Appl. No. 11/967,897 dated Mar. 10, 2011.

\* cited by examiner

ASYMMETRIC CYANINE FLUORESCENT DYES, COMPOSITIONS AND THEIR USE IN STAINING BIOLOGICAL SAMPLES

RELATED APPLICATIONS

This application claims priority to Chinese Patent Application No. 200810002503.7, filed Jan. 4, 2008, for "ASYMMETRIC CYANINE FLUORESCENT DYES, COMPOSITIONS COMPRISING THE SAME AND THEIR USE IN STAINING BIOLOGICAL SAMPLES," the disclosure of which is fully incorporated herein by reference.

TECHNICAL FIELD

The present disclosure relates to fluorescent dyes. More particularly, the present disclosure relates to asymmetric cyanine fluorescent dyes useful in staining biological samples, compositions comprising the same and their use in staining biological samples.

BRIEF SUMMARY

Asymmetric cyanine fluorescent dyes are disclosed. Compositions including asymmetric cyanine fluorescent dyes and their use in staining biological samples are also disclosed.

DETAILED DESCRIPTION

The incorporation and rapid development of new sciences and technologies such as lasers, microprocessors and electronics have promoted the application of fluorescent analysis techniques. Particularly, with the advent of biochips having fluorescent dyes as the labeling agent, the fluorescent analysis techniques find wide application in cell immunology, microbiology, molecular biology, molecular genetics, pathology, clinical laboratory science, and botany, among others. The development of fluorescent dyes plays a pivotal role in the progress of fluorescent analysis techniques.

Early-used dyes include new methylene blue (NMB), brilliant cresyl blue (BCB), pyronin Y and ethidium bromide, etc. They form complexes with nucleic acid molecules through intercalation or electrostatic attraction and therefore enhanced fluorescence can be observed under a microscope. However, these dyes can form dye complexes by themselves that are not distinctly distinguished from the complexes formed with nucleic acids, resulting in strong background interference in fluorescence. Also, these dyes have a low fluorescence quantum efficiency, which decreases the degree of fluorescent enhancement and affects the accuracy of detection results.

Acridine orange is also used in fluorescent analysis by virtue of the fluorescence-enhancing complexes that it forms with nucleic acids. But these kinds of dye molecules may cause optical quenching among each other in the process of energy transfer, which results in the dye-nucleic acid complexes emitting no fluorescent and therefore influences the authenticity of detection results. Acridine orange may also have a strong interaction with the plastic tubings in flow cytometers, leading to increased intensity of background fluorescence. A longer time of washing of the tubings in the instruments is required for cleaning the post-detection residual dyes and ensuring the accuracy of detection results, and thus reduces the analyzing efficiency of the instruments.

U.S. Pat. No. 4,957,870 discloses a thiazole blue dye useful in the detection of nucleic acids and blood reticulocytes. The excitation wavelength of this dye is 488 nm, which requires a costly laser as the light source, and therefore increases the cost in equipment. Moreover, this kind of dye requires a longer incubation time to better bind to nucleic acids.

U.S. Pat. No. 5,994,138 discloses a dye for staining blood reticulocytes. This dye requires a reaction condition of above 35° C. to bring good detection results, which poses a higher demand on the use conditions of instruments.

Although cyanine fluorescent dyes in current use such as TOTAB, TOTIN, TO-PRO-3, PO-PRO-2 and BO-PRO-2 or the like [K. M. Sovenyhazy, J. A. Bordelon, J. T. Petty. Nucleic Acids Res, 2003, 31, 2561] have absorption and emission wavelengths that are both in the near-infrared region (670-1000 nm), their complex molecular structures, long synthesis routes and low synthesis yields and therefore high price limit their scope of use.

Therefore, it would be desirable to develop novel fluorescent dyes which may include one or more of the following attributes: (1) they do not fluoresce when unbound to nucleic acids but have a high fluorescence quantum yield when bound to nucleic acids; (2) they have a light spectrum in the near-infrared region so that interference from background fluorescence can be avoided; (3) they can be excited near 633 nm so that low-price lasers can be used as the light source; (4) they have a certain level of water solubility together with a certain ability to penetrate cell membranes.

In one embodiment there is provided a compound having the structure of the following general formula I:

wherein
n is 1, 2 or 3;
X is C(CH$_3$)$_2$, O, S or Se;

$R_1$ and $R_2$ are each independently selected from at least one of the following: H, OH, $C_{1-18}$alkyl, $C_{1-6}$alkyl-$OR_5$, $C_{1-18}$alkylsulfo, phenyl and halogen;

$R_3$ and $R_4$ are each independently selected from at least one of the following: $C_{1-18}$alkyl-$COOR_6$, $C_{1-18}$alkyl-$OR_6$, and benzyl, wherein said benzyl is optionally substituted with one or more substituents selected from at least one of the following: halogen, hydroxyl, sulfhydryl, cyano, nitro, alkyl, aryl, alkoxy, heterocyclyl, haloalkyl, amino, alkylamino, amido and carboxyl, provided that $R_3$ and $R_4$ are not simultaneously benzyl, and $R_4$ is not $C_{1-18}$alkyl-$OR_6$ when $R_3$ is benzyl;

$R_5$ is $C_{1-18}$alkyl or H;

$R_6$ is $C_{1-18}$alkyl, H or phenyl, wherein said phenyl is optionally substituted with one or more substituents selected from at least one of the following: halogen, hydroxyl, sulfhydryl, cyano, nitro, alkyl, aryl, alkoxy, heterocyclyl, haloalkyl, amino, alkylamino, amido and carboxyl; and $Y^-$ is an anion.

In another aspect there is provided a conjugate comprising the compounds of the above formula I.

In yet another aspect there is provided a composition useful in staining biological samples, said composition comprising the compounds of the above formula I or conjugates thereof.

In still another aspect there is provided a use of the compounds of the above formula I or conjugates or compositions thereof in staining biological samples.

The compounds, conjugates or compositions disclosed may stain biological samples such as nucleic acids, leucocytes, erythroblasts, reticulocytes and the like, and the complexes thus formed have an emission wavelength in the near-infrared region, which avoids the interference from background fluorescence of the organisms per se, improves the accuracy of detection results and permits their use on a flow cytometer as the staining agent for various biological samples.

Definitions

Unless otherwise specified, the following terms as used herein have the following meanings.

The term "alkyl" as used herein individually or in combination with other groups refers to straight or branched alkyl groups containing 1-18 carbon atoms, such as 1-12, or alternatively 1-8, or 1-6 carbon atoms. Reference to a single alkyl such as "n-propyl" specifically means a straight alkyl group, while reference to a single branched alkyl such as "isopropyl" specifically means a branched alkyl group. For example, "$C_{1-6}$alkyl" includes $C_{1-4}$alkyl, $C_{1-3}$alkyl, methyl, ethyl, n-propyl, isopropyl and tert-butyl. The like rules also apply to other groups as used throughout the present specification.

The term "alkoxy" as used herein refers to the "alkyl" as defined above in combination with the group —O—, wherein said "alkyl" contains 1-18 carbon atoms, such as 1-12, or alternatively 1-8, or 1-6 carbon atoms, such as methoxy, ethoxy, propoxy and the like.

The term "halogen" as used herein includes fluorine, chlorine, bromine and iodine.

The term "benzyl" as used herein refers to —$CH_2$-Ph group. Modification of a benzyl group by the phrase "optionally substituted with" means that the benzyl group either can exist in an unsubstituted form, or can be substituted with a suitable substituent at any suitable position. Suitable substituents include, but are not limited to, halogen, hydroxyl, sulfhydryl, cyano, nitro, alkyl, aryl, alkoxy, heterocyclyl, haloalkyl, amino, alkylamino, amido, carboxyl, etc., so long as the compounds finally formed have the properties as contemplated by the present disclosure. In one embodiment, the benzyl group is optionally substituted with halogen, hydroxyl, sulfhydryl, cyano, nitro or amino.

The term "heterocyclyl" as used herein refers to a single ring or fused ring system comprising 3-14 ring members, such as 3-10, or alternatively 3-6 ring members and containing one or more heteroatoms selected from nitrogen, oxygen and sulfur.

The term "biological sample" as used herein includes but is not limited to nucleic acids and leucocytes, erythroblasts, and reticulocytes in the blood, etc.

Exemplary Compounds

In one embodiment a compound has the structure of the following general formula I:

wherein n is 1, 2 or 3;

X is $C(CH_3)_2$, O, S or Se;

$R_1$ and $R_2$ are each independently selected from at least one of the following: H, OH, $C_{1-18}$alkyl, $C_{1-6}$alkyl-$OR_5$, $C_{1-18}$alkylsulfo, phenyl and halogen;

$R_3$ and $R_4$ are each independently selected from at least one of the following: $C_{1-18}$alkyl-$COOR_6$, $C_{1-18}$alkyl-$OR_6$, and benzyl, wherein said benzyl is optionally substituted with one or more substituents selected from at least one of the following: halogen, hydroxyl, sulfhydryl, cyano, nitro, alkyl, aryl, alkoxy, heterocyclyl, haloalkyl, amino, alkylamino, amido and carboxyl, provided that $R_3$ and $R_4$ are not simultaneously benzyl, and $R_4$ is not $C_{1-18}$alkyl-$OR_6$ when $R_3$ is benzyl;

$R_5$ is $C_{1-18}$alkyl or H;

$R_6$ is $C_{1-18}$alkyl, H or phenyl, wherein said phenyl is optionally substituted with one or more substituents selected from at least one of the following: halogen, hydroxyl, sulfhydryl, cyano, nitro, alkyl, aryl, alkoxy, heterocyclyl, haloalkyl, amino, alkylamino, amido and carboxyl; and $Y^-$ is an anion.

In one embodiment n is 1 or 2, and in another n is 1.

In one embodiment X is $C(CH_3)_2$, O or S; or alternatively, X is $C(CH_3)_2$ or S; or X is S.

In one embodiment $R_1$ and $R_2$ are each independently selected from at least one of the following: H and $C_{1-18}$alkyl; alternatively, $R_1$ and $R_2$ are each independently selected from at least one of the following: H and $C_{1-6}$alkyl; and in yet another embodiment $R_1$ and $R_2$ are both H.

In one embodiment, $R_3$ and $R_4$ are each independently selected from at least one of the following: $C_{1-8}$alkyl-$COOR_6$, $C_{1-8}$alkyl-$OR_6$, and benzyl, wherein said benzyl is optionally substituted with one or more substituents selected from at least one of the following: halogen, hydroxyl, sulfhydryl, cyano, nitro and amino. Alternatively, $R_3$ and $R_4$ are each independently selected from at least one of the following: $C_{1-6}$alkyl-$COOR_6$, $C_{1-6}$alkyl-$OR_6$, and benzyl, wherein said benzyl is optionally substituted with one or more substituents selected from at least one of the following: halogen, hydroxyl, sulfhydryl, cyano, nitro and amino. In another embodiment, $R_5$ is H or $C_{1-12}$alkyl, or alternatively, $R_5$ is H or $C_{1-6}$alkyl.

In one embodiment, $R_6$ is $C_{1-6}$alkyl or phenyl, wherein said phenyl is optionally substituted with one or more substituents selected from at least one of the following: halogen, hydroxyl, sulfhydryl, cyano, nitro, alkyl, aryl, alkoxy, heterocyclyl, haloalkyl, amino, alkylamino, amido and carboxyl.

$Y^-$ represents an anion, which can be any suitable anion, including but not limited to inorganic anions or organic anions, such as halogen ions, $ClO_4^-$, $PF_6^-$, $CF_3SO_3^-$, $BF_4^-$, acetate or p-toluenesulfonate anions.

The compounds disclosed can be directly used for staining biological samples in the form of salts as described herein.

Alternatively, in one embodiment, the compounds disclosed can exist in the form of derivatives of the compounds of formula I, said derivatives including, but not limited to, conjugates.

Subsequently or simultaneously with mixing a red blood cell lysing agent, the stock solution of the fluorescent dye is added to fluorescently label the white blood cells. When the blood sample is mixed with the reagent disclosed herein, the total volume of the blood sample and the reagent may ensure that a sufficient concentration of cells will pass through the detection channel of the apparatus. The reagent composition may dilute the blood sample to a proportion of 10:1, 50:1 or 100:1, or any value in any of the above ranges, so long as the dilution meets the requirements of practical use. Such adjustment is within the capability of those skilled in the art with the aid of the present disclosure.

Typically, conjugates are used in the fluorescence activated cell sorter (FACS). "Conjugates" as used herein refer to the compounds formed by attaching the fluorescent dyes disclosed to other molecules via covalent bonds. Molecules that can be conjugated with the fluorescent dyes disclosed may be those that specifically bind to cells or cell components, including, but not limited to, antibodies, antigens, receptors, ligands, enzymes, substrates, coenzymes or the like. Generally, the test sample is incubated with the fluorescent conjugates for a period of time so that the fluorescent conjugates bind specifically to certain cells or cell components in the test sample. The binding of the fluorescent conjugates to the cells or cell components is also referred to as staining. The staining step can be repeated in sequence several times, or a variety of conjugates can be used for concurrent multistaining. After staining, analysis of the sample is conducted in the fluorescence activated cell sorter, wherein the excitation light source excites the fluorescent dyes disclosed in the conjugates and the detection apparatus detects the emitted light generated by the excited fluorescent dyes.

Alternatively, in another embodiment, the fluorescent conjugates can also be used in solid phase immunological assays, e.g., in sandwich immunological assays. The techniques for solid phase immunological assays are well known in the art and can be found in standard textbooks. The fluorescent conjugates disclosed can be used as the various suitable components in solid phase immunological assays.

Methods for Preparing Exemplary Compounds

The compounds disclosed can be prepared using general methods known in the art. See, for example, Chinese Patent Application CN200710137258.6, which is incorporated herein by reference. In particular, the asymmetric cyanine fluorescent dyes disclosed are generally synthesized by the following steps. First, react unsubstituted or substituted 2-methylbenzothiazole, 2-methylbenzoxazole or 2,3,3-trimethyl-3H-indoline as the starting material with a halide of formula $R_3X$ (X is F, Cl, Br or I) in a molar ratio of 1:1-2 by refluxing in toluene for 12-36 hours to obtain the quaternary ammonium salt intermediates of formula II:

wherein X, $R_1$, $R_3$ and $Y^-$ are as defined in the compounds of the above formula I.

Next, condense the resulting quaternary ammonium salt intermediates of formula II with linking molecules to obtain the compounds of formula III:

wherein X, n, $R_1$, $R_3$ and $Y^-$ are as defined in the compounds of formula I, and the linking molecules can be N,N'-diphenylformamidine or higher homologues thereof.

Then, obtain substituted or unsubstituted 4-methylquinolinium salt intermediates in a process similar to that used in the synthesis of the compounds of formula II. Finally, reflux the 4-methylquinolinium salt intermediates with the compounds of formula III in pyridine or acetic anhydride to obtain the desired asymmetric cyanine fluorescent dyes. The resulting fluorescent dyes can be recovered using separation and purification techniques well known in the art to achieve the desired purity.

The raw materials used in the present disclosure are commercially available, or can be readily prepared from raw materials known in the art using methods known to those skilled in the art or methods disclosed in the art.

It is appreciated that certain of the various ring substituents in the compounds disclosed may be introduced through standard aromatic substitution reactions or generated by conventional functional group modifications either prior to or immediately following the processes mentioned above, and as such are included in the process disclosed. Such reactions and modifications include, for example, introduction of a substituent by means of an aromatic substitution reaction, reduction of substituents, alkylation of substituents and oxidation of substituents. The reagents and reaction conditions for such procedures are well known in the chemical arts. Particular examples of aromatic substitution reactions include the introduction of a nitro group using concentrated nitric acid, the introduction of an acyl group using, for example, an acyl halide and Lewis acid (such as aluminum trichloride) under Friedel Crafts conditions; the introduction of an alkyl group using an alkyl halide and Lewis acid (such as aluminum trichloride) under Friedel Crafts conditions; and the introduction of a halogen group. Particular examples of modifications include the reduction of a nitro group to an amino group by, for example, catalytic hydrogenation with a nickel catalyst or treatment with iron in the presence of hydrochloric acid with heating; oxidation of alkylthio to alkylsulphinyl or alkylsulphonyl.

The fluorescent conjugates comprising the compounds of formula I can be synthesized using any conventional methods known in the art.

Exemplary Compositions

The present disclosure also provides compositions comprising the above-mentioned compounds of formula I or conjugates thereof, which are used for staining biological samples The solution may be finally adjusted to about pH 7.

The compositions may comprise, besides the compounds of formula I or conjugates thereof, other components required for staining biological samples, e.g., solvents, osmotic regulating agents, pH regulating agents, surfactants, etc. The compositions may exist in the form of an aqueous solution, or in other suitable forms that can be formulated into solution using water prior to usage.

Usage of the Exemplary Compounds or Compositions

The present disclosure further provides a method for staining biological samples using the above-mentioned compounds of the formula I or conjugates thereof, or compositions comprising the above-mentioned compounds of formula I or conjugates thereof. The method may include the step of contacting the above-mentioned compounds of formula I or conjugates thereof, or the compositions comprising the above-mentioned compounds of formula I or conjugates thereof with the biological samples. The term "contacting" as used herein may include contacting in solution or in solid phase.

Characteristics

From the above description and common knowledge familiar to those skilled in the art, the various characteristics of the fluorescent dyes disclosed may include, but are not limited to the following: (1) The compounds provided may stain DNA, and the dye/DNA complexes formed have a fluorescence emission strength 40-100 times higher than that of the dyes themselves. (2) The compounds provided also stain RNA, and the dye/RNA complexes formed have a fluorescence emission strength 20-40 times higher than that of the dyes themselves. (3) The dye/nucleic acid complexes may have an emission wavelength in the range of 640 nm-900 nm in the near-infrared region, which avoids interference from the background fluorescence of the organisms per se and may improve the accuracy of detection results. (4) The compounds provided may be used on a flow cytometer as the staining agent for reticulocytes, leucocyte and erythroblast in the blood. (5) The compounds provided, when bound to nucleic acids, may be excited by 633-nm wavelength light emitted by a red semiconductor laser, thereby reducing the equipment cost.

EXAMPLES

The present disclosure is further illustrated by the following particular examples to which or by which the present disclosure is not limited, as is appreciated by one skilled in the art.

Example 1

Synthesis of Dye-1

In a mixed solution of 40 mL of methanol and 20 mL of ethanol, 10 mmol of 1-ethyl hexanoate-2-methylbenzothiazolium bromide and 30 mmol of N,N'-diphenylformamidine were heated while stirring in a 65° C. oil bath for 6 hours. After the reaction was completed, the solvents were distilled off under reduced pressure. Then an amount of ethyl ether was added and stirred to precipitate orange solid powder which was then filtered and dried. The crude product was recrystallized in ethyl acetate-hexane to obtain an orange-red solid product with a yield of 42%. Into 4.0 mmol of the obtained reaction product were added 4.2 mmol of 1-benzyl-4-methylquinolinium salt and 10 ml of pyridine, and the mixture was heated while stirring in a 90° C. oil bath for 1.5 hours. The reaction was cooled down to room temperature and then poured into ethyl ether to precipitate dark purple-red solids which were then filtered and dried. The dye was separated through a silica column using dichloromethane:methanol=100:10 as the eluent. The blue fractions were collected and dried in a vacuum drying oven at 45° C. for 24 hours to obtain the exemplary Dye-1 compound in a yield of 53%. MS (EI) $C_{34}H_{35}BrN_2O_2S$ m/z: 535.2 [M-Br]$^+$.

Example 2

Synthesis of Dye-2

In a mixed solution of 40 mL of methanol and 20 mL of ethanol, 10 mmol of 1-(2-hydroxyethyl)-2-methylbenzothiazolium bromide and 30 mmol of N,N'-diphenylformamidine were heated while stirring in a 65° C. oil bath for 6 hours. After the reaction was completed, the solvents were distilled off under reduced pressure. Then an amount of ethyl ether was added and stirred to precipitate orange solid powder which was filtered and dried. The crude product was recrystallized in ethyl acetate-hexane to afford an orange-red solid product with a yield of 41%. Into 4.0 mmol of the obtained reaction product were added 4.5 mmol of 1-ethyl butanoate-4-methylquinolinium salt and 10 ml of pyridine, and the mixture was heated while stirring in a 90° C. oil bath for 1.5 hours. The reaction was cooled down to room temperature and then poured into ethyl ether to precipitate purple-red solids which were then filtered and dried. The dye was separated through a silica column using dichloromethane:methanol=100:18 as the eluent. The blue fractions were collected and dried in a vacuum drying oven at 45° C. for 24 hours to obtain the exemplary Dye-2 compound in a yield of 49%. MS (EI) $C_{27}H_{29}BrN_2O_3S$: m/z: 461.2[M-Br]$^+$.

Example 3

Preparation of Dye-3

In a mixed solution of 40 mL of methanol and 20 mL of ethanol, 10 mmol of 1-(2-phenoxyethyl)-2-methylbenzothiazolium bromide and 30 mmol of N,N'-diphenylformamidine were heated while stirring in a 65° C. oil bath for 5 hours. After the reaction was completed, the solvents were distilled off under reduced pressure. Then an amount of ethyl ether was added and stirred to precipitate orange solid powder which was then filtered and dried. The crude product was recrystallized in ethyl acetate-hexane to afford an orange-red solid product with a yield of 47%. Into 4.0 mmol of the obtained reaction product were added 4.2 mmol of 1-(2-hydroxyethyl)-4-methylquinolinium salt and 10 ml of pyridine, and the mixture was heated while stirring in a 90° C. oil bath for 1.5 hours. The reaction was cooled down to room temperature and then poured into ethyl ether to precipitate purple-red solids which were then filtered and dried. The dye was separated through a silica column using dichloromethane:methanol=100:15 as the eluent. The blue fractions were collected and dried in a vacuum drying oven at 45° C. for 24 hours to obtain the exemplary Dye-3 compound in a yield of 40%. MS (EI) $C_{29}H_{27}BrN_2O_2S$ m/z: 467.2 [M-Br]$^+$.

Example 4

Preparation of Dye-4

In a mixed solution of 40 mL of methanol and 20 mL of ethanol, 10 mmol of 1-ethyl butanoate-2-methylbenzothiazolium bromide and 30 mmol of N,N'-diphenylformamidine were heated while stirring in a 65° C. oil bath for 6 hours. After the reaction was completed, the solvents were distilled off under reduced pressure. Then an amount of ethyl ether was added and stirred to precipitate orange solid powder which was filtered and dried. The crude product was recrystallized in ethyl acetate-hexane to afford an orange-red solid product with a yield of 40%. Into 4.0 mmol of the obtained reaction product were added 4.2 mmol of 1-(4-methoxyphenyl)-4-methylquinolinium salt and 10 ml of pyridine, and the mixture was heated while stirring in a 90° C. oil bath for 1.5 hours. The reaction was cooled down to room temperature and then poured into ethyl ether to precipitate purple-red solids which were then filtered and dried. The dye was separated through a silica column using dichloromethane:methanol=100:8 as the eluent. The blue fractions were collected and dried in a vacuum drying oven at 45° C. for 24 hours to obtain the exemplary Dye-4 compound in a yield of 61%. MS (EI) $C_{33}H_{33}BrN_2O_3S$ m/z: 537.2[M-Br]$^+$.

Example 5

Preparation of Dye-5

In a mixed solution of 40 mL of methanol and 20 mL of ethanol, 10 mmol of 1-ethyl butanoate-2-methylbenzothiazolium bromide and 30 mmol of N,N'-diphenylformamidine were heated while stirring in a 65° C. oil bath for 6 hours. After the reaction was completed, the solvents were distilled off under reduced pressure. Then an amount of ethyl ether was added and stirred to precipitate orange solid powder which was then filtered and dried. The crude product was recrystallized in ethyl acetate-hexane to obtain an orange-red solid product in a yield of 40%. Into 4.0 mmol of the obtained reaction product were added 4.2 mmol of 1-(4-fluorophenyl)-4-methylquinolinium salt and 10 ml of pyridine, and the mixture was heated while stirring in a 90° C. oil bath for 1.5 hours. The reaction was cooled down to room temperature and then poured into ethyl ether to precipitate purple-red solids which were then filtered and dried. The dye was separated through a silica column using dichloromethane:methanol=100:8 as the eluent. The blue fractions were collected and dried in a vacuum drying oven at 45° C. for 24 hours to obtain the exemplary Dye-5 compound in a yield of 49%. MS (EI) $C_{32}H_{30}BrFN_2O_2S$ m/z: 525.2 [M-Br]$^+$.

Example 6

Preparation of Dye-6

In a mixed solution of 40 mL of methanol and 20 mL of ethanol, 10 mmol of 1-ethyl butanoate-2-methylbenzothiazolium bromide and 30 mmol of N,N'-diphenylformamidine were heated while stirring in a 65° C. oil bath for 6 hours. After the reaction was completed, the solvents were distilled off under reduced pressure. Then an amount of ethyl ether was added and stirred to precipitate orange solid powder which was then filtered and dried. The crude product was recrystallized in ethyl acetate-hexane to obtain an orange-red solid product with a yield of 40%. Into 4.0 mmol of the obtained reaction product were added 4.2 mmol of 1-(2-hydroxyethyl)-4-methylquinolinium salt and 10 ml of pyridine, and the mixture was heated while stirring in a 90° C. oil bath for 1.5 hours. The reaction was cooled down to room temperature and then poured into ethyl ether to precipitate purple-red solids which were then filtered and dried. The dye was separated through a silica column using dichloromethane:methanol=100:14 as the eluent. The blue fractions were collected and dried in a vacuum drying oven at 45° C. for 24 hours to obtain the exemplary Dye-6 compound in a yield of 43%. MS (EI) $C_{27}H_{29}N_2O_3S$ m/z: 461.2 [M-Br]$^+$.

Example 7

Preparation of Dye-7

In a mixed solution of 40 mL of methanol and 20 mL of ethanol, 10 mmol of 1-(2-phenoxyethyl)-2-methylbenzothiazolium bromide and 30 mmol of N,N'-diphenylformamidine were heated while stirring in a 65° C. oil bath for 5 hours. After the reaction was completed, the solvents were distilled off under reduced pressure. Then an amount of ethyl ether was added and stirred to precipitate orange solid powder which was then filtered and dried. The crude product was recrystallized in ethyl acetate-hexane to obtain an orange-red solid product in a yield of 47%. Into 4.0 mmol of the obtained reaction product were added 4.2 mmol of 1-benzyl-4-methylquinolinium salt and 10 ml of pyridine, and the mixture was heated while stirring in a 90° C. oil bath for 1.5 hours. The reaction was cooled down to room temperature and then poured into ethyl ether to precipitate dark purple-red solids which were then filtered and dried. The dye was separated through a silica column using dichloromethane:methanol=100:10 as the eluent. The blue fractions were collected and dried in a vacuum drying oven at 45° C. for 24 hours to obtain the exemplary Dye-7 compound in a yield of 46%. MS (EI) $C_{34}H_{29}BrN_2OS$ m/z:513.2[M-Br]$^+$.

Example 8

Preparation of Dye-8

In a mixed solution of 40 mL of methanol and 20 mL of ethanol, 10 mmol of 1-(2-phenoxyethyl)-2-methylbenzothiazolium bromide and 30 mmol of N,N'-diphenylformamidine were heated while stirring in a 65° C. oil bath for 5 hours. After the reaction was completed, the solvents were distilled off under reduced pressure. Then an amount of ethyl ether was added and stirred to precipitate orange solid powder which was then filtered and dried. The crude product was recrystallized in ethyl acetate-hexane to obtain an orange-red solid product with a yield of 47%. Into 4.0 mmol of the obtained reaction product were added 4.5 mmol of 1-(4-methoxyphenylethyl)-4-methylquinolinium salt and 10 ml of pyridine, and the mixture was heated while stirring in a 90° C. oil bath for 1.5 hours. The reaction was cooled down to room temperature and then poured into ethyl ether to precipitate purple-red solids which were then filtered and dried. The dye was separated through a silica column using dichloromethane:methanol=100:7 as the eluent. The blue fractions were collected and dried in a vacuum drying oven at 45° C. for 24 hours to obtain the exemplary Dye-8 compound in a yield of 51%. MS (EI) $C_{35}H_{31}BrN_2O_2S$ m/z: 543.2 [M-Br]$^+$.

Example 9

Preparation of Dye-9

In 20 ml of solvents (acetic acid: acetic anhydride=1:1), 8 mmol of 1-(2-phenoxyethyl)-2-methylbenzothiazolium bromide and 10 mmol of malonaldehyde diphenylimine hydrochloride were heated to 120° C. for 1 hour. Then the reaction mixture was cooled and ethyl ether was added to precipitate solids. The solids were filtered and washed with 30 mL of ethyl acetate three times to remove the excess unreacted condensing agent. Then the solids were dried to give brown-yellow powder with a crude yield of 68%. Into 4.0 mmol of the obtained reaction product were added 6 mmol of 1-(2-hydroxyethyl)-4-methylquinolinium salt and 10 ml of pyridine, and the mixture was heated while stirring in a 110° C. oil bath for 1 hour. The reaction was cooled and then poured into ethyl ether to precipitate small dark purple particles which were then filtered and dried. The dye was separated through a silica column using dichloromethane:methanol=100:15 as the eluent. The blue fractions were collected and dried in a vacuum drying oven at 45° C. for 24 hours to obtain the exemplary Dye-9 compound in a yield of 43%. MS (EI) $C_{31}H_{29}BrN_2O_2S$: m/z: 493.2 $[M-Br]^+$.

Example 10

Figure 1:
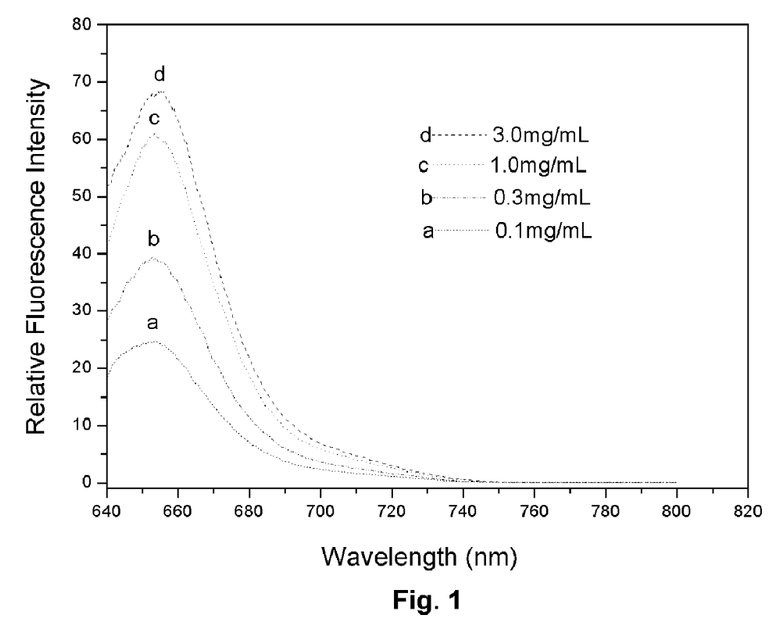
FIG. 1 is the fluorescence emission spectra for Dye-1 in phosphate buffered solution (PBS) after it binds with various concentrations of salmon sperm DNA.

Detection of the Fluorescence Intensity of Dye-1 in Phosphate Buffered Saline (PBS) Containing Different Concentrations of DNA An amount of Dye-1 was accurately weighed and sufficiently dissolved in 2.5 mL methanol/ethylene glycol (50:50 vol/vol) to prepare a dye solution at a concentration of 5 mM. This solution was filtered before use. Separate amounts of salmon sperm DNA were weighed and dissolved in PBS to obtain PBS buffers containing 3 mg/mL, 1 mg/mL, 0.3 mg/mL, 0.1 mg/mL of DNA. 2-µL aliquots of the prepared 5 mM dye solution were accurately measured and respectively combined in 1 mL PBS with 1 µL of the PBS buffers containing different concentrations of DNA. After reacting for a period of time, the complexes were detected for their emission spectra at the selected excitation wavelength of 633 nm. The detection temperature was at room temperature. The instrument used was fluorescence spectrophotometer Model FL-4500. The results were as shown in FIG. 1. It can be seen from the figure that the fluorescence emission strength of the dye/DNA complexes increased rapidly with the increase in DNA concentration.

Figure 2:
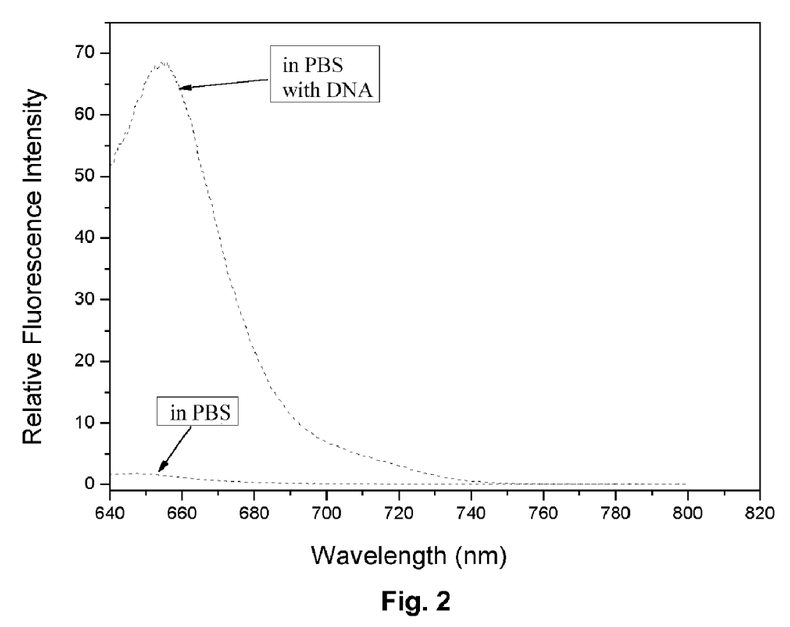
FIG. 2 is the fluorescence emission spectra for Dye-1 in PBS before and after it binds with salmon sperm DNA.

FIG. 2 is a comparison of the relative fluorescence strength of Dye-1 in PBS before and after it is bound with DNA. As can be seen from the figure, Dye-1 scarcely generated any fluorescence in PBS without DNA, but when it formed complexes with DNA the fluorescence intensity increased rapidly, with the maximum excitation peak at about 654 nm in the near-infrared region, which can avoid the interference from the background fluorescence of the organisms themselves.

Example 11

Figure 3:
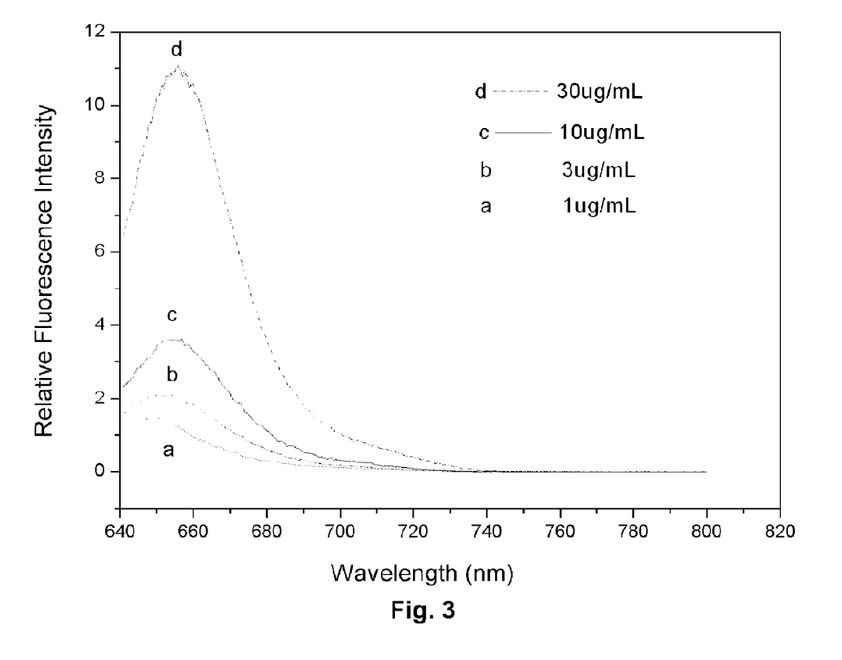
FIG. 3 is the fluorescence emission spectra for Dye-1 in PBS after it binds with various concentrations of soft-shelled turtle (*Trionyx sinensis*) liver RNA.

Detection of the Fluorescence Intensity of Dye-1 in PBS Containing Different Concentrations of RNA An amount of Dye-1 was accurately weighed and sufficiently dissolved in 2.5 mL methanol/ethylene glycol (50:50 vol/vol) to prepare a dye solution at a concentration of 5 mM. This solution was filtered before use. Separate amounts of soft-shelled turtle (*Trionyx sinensis*) liver RNA were weighed and dissolved in PBS to obtain PBS buffers containing 30 µg/mL, 10 µg/mL, 3 µg/mL, 1 µg/mL of RNA. 2-µL aliquots of the prepared 5 mM dye solution were accurately measured and respectively combined in 1 mL PBS with 1 µL of the PBS buffers containing different concentrations of RNA. After reacting for a period of time, the complexes were detected for their emission spectra at the selected excitation wavelength of 633 nm. The detection temperature was at room temperature. The instrument used was fluorescence spectrophotometer Model FL-4500. The results were as shown in FIG. 3. It can be seen from the figure that the fluorescence emission strength of the dye/RNA complexes likewise increased rapidly with the increase in RNA concentration.

Figure 4:
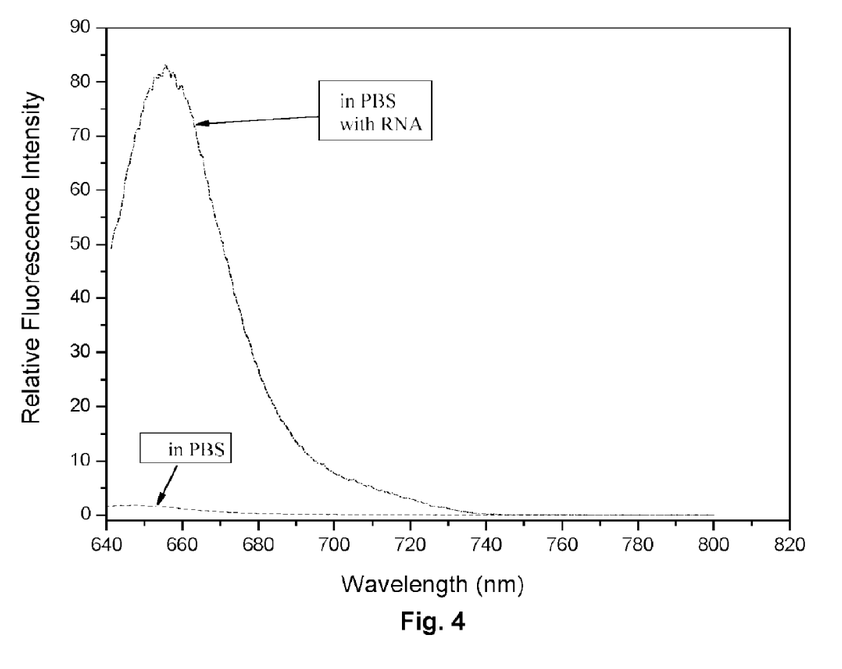
FIG. 4 is the fluorescence emission spectra for Dye-1 in PBS before and after it binds with soft-shelled turtle (*Trionyx sinensis*) liver RNA.

FIG. 4 is a comparison of the relative fluorescence strength of Dye-1 in PBS before and after it is bound with RNA. As can likewise be seen in the figure, when Dye-1 formed complexes with RNA, there occurred a rapid increase in fluorescence intensity accompanied by a certain degree of red shift of fluorescence, with the maximum excitation peak at about 655 nm in the near-infrared region, which can avoid the interference from the background fluorescence of the organisms per se and therefore improve the accuracy of detection.

Example 12

Figure 5:
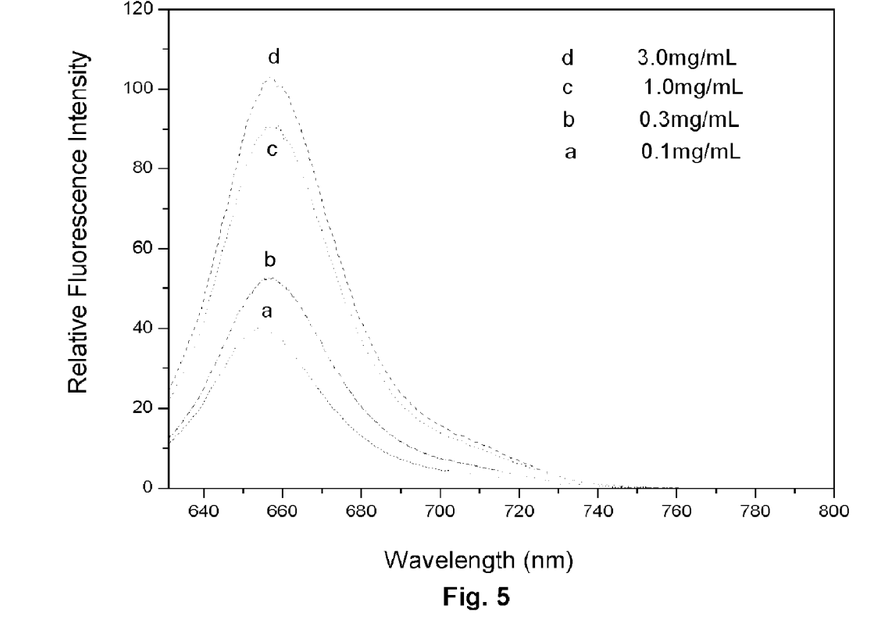
FIG. 5 is the fluorescence emission spectra for Dye-2 in PBS after it binds with various concentrations of salmon sperm DNA.
Figure 6:
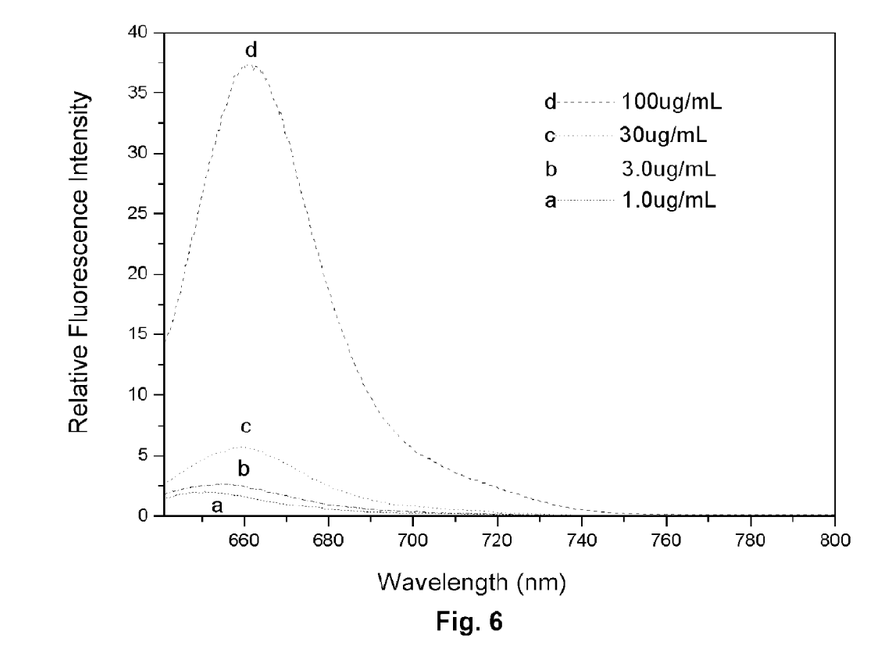
FIG. 6 is the fluorescence emission spectra for Dye-2 in PBS after it binds with various concentrations of soft-shelled turtle (*Trionyx sinensis*) liver RNA.
Figure 7:
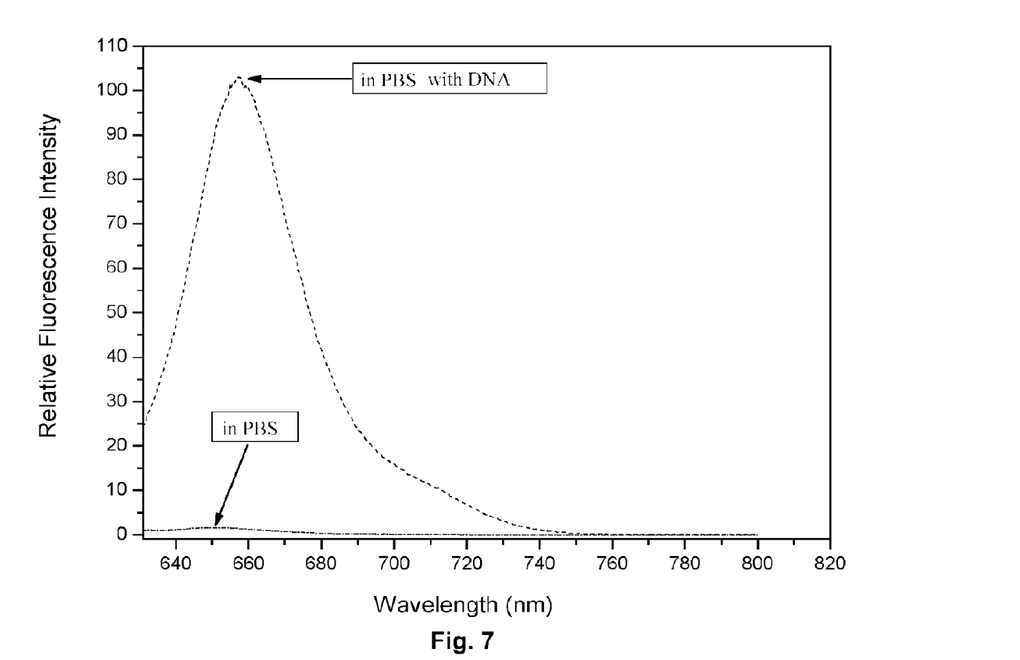
FIG. 7 is the fluorescence emission spectra for Dye-2 in PBS before and after it binds with salmon sperm DNA.
Figure 8:
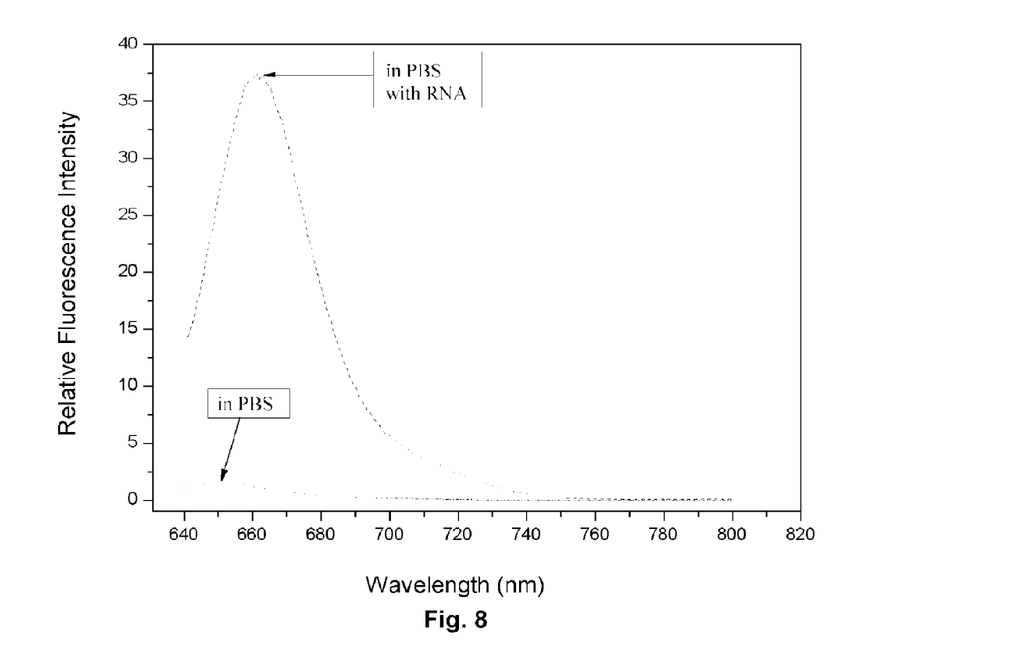
FIG. 8 is the fluorescence emission spectra for Dye-2 in PBS before and after it binds with soft-shelled turtle (*Trionyx sinensis*) liver RNA.

Detection of the Fluorescence Intensity of Dye-2 in PBS Containing Different Concentrations of DNA/RNA The detection procedures followed were those described in Example 10 and Example 11. The fluorescence spectra for the complexes of Dye-2 with different concentrations of DNA or RNA are shown in FIG. 5 and FIG. 6, respectively. The comparisons of fluorescence for Dye-2 before and after it is bound with DNA or with RNA in PBS are shown in FIG. 7 and FIG. 8, respectively. As can be seen from the figures, the dye per se scarcely generated any fluorescence, but when it formed complexes with the added nucleic acids the fluorescence intensities likewise increased rapidly, with the maximum excitation peaks all beyond 650 nm.

Example 13

Figure 9:
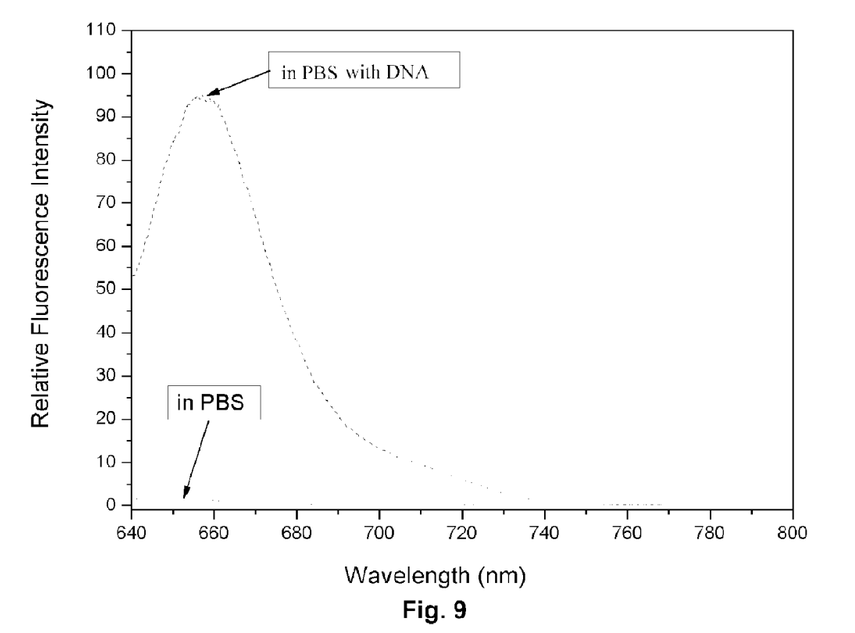
FIG. 9 is the fluorescence emission spectra for Dye-3 in PBS before and after it binds with salmon sperm DNA.
Figure 10:
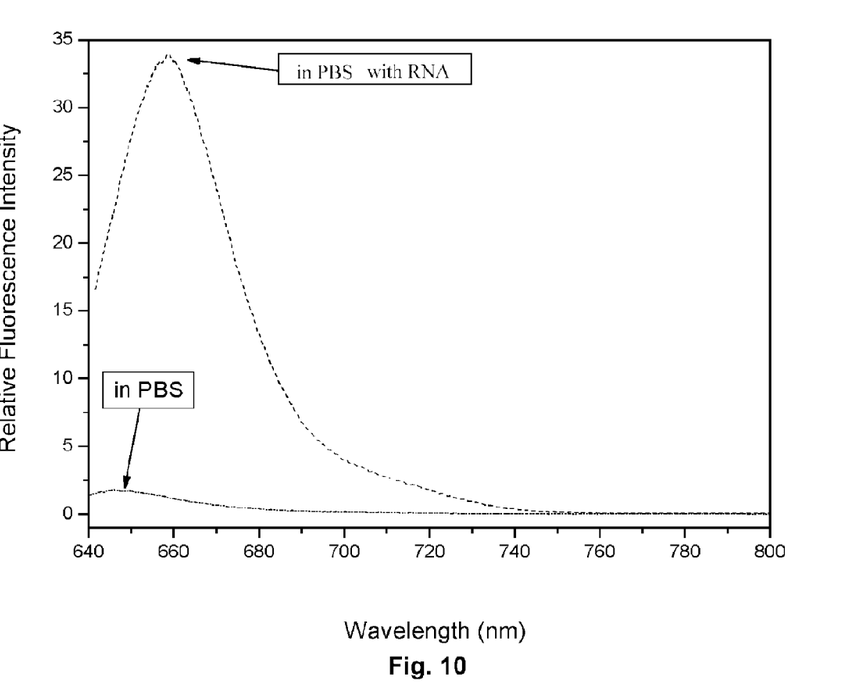
FIG. 10 is the fluorescence emission spectra for Dye-3 in PBS before and after it binds with soft-shelled turtle (*Trionyx sinensis*) liver RNA.

Detection of the Fluorescence Intensity of Dye-3 in PBS Containing Different Concentrations of DNA/RNA The detection procedures followed were those described in Example 10 and Example 11. The comparisons of fluorescence for Dye-3 before and after it bound with DNA or with RNA in PBS are shown in FIG. 9 and FIG. 10, respectively. As can be seen from the figures, the dye per se generated weak fluorescence in PBS, but when it formed complexes with the added DNA or RNA the fluorescence intensities markedly increased, with the maximum excitation peaks all beyond 650 nm.

Table 1 compares the ratios of increase in fluorescence for Dye-1, Dye-2 and Dye-3 after vs before they bound with salmon sperm DNA in PBS.

TABLE 1

| Dye | Relative fluorescence intensity | | Ratio of increase in fluorescence (after vs before binding) |
|---|---|---|---|
| | Before binding DNA | After binding DNA | |
| Dye-1 | 1.82 | 68.63 | 38 |
| Dye-2 | 0.97 | 102.93 | 106 |
| Dye-3 | 1.64 | 94.37 | 55 |

Table 2 compares the ratios of increase in fluorescence for Dye-1, Dye-2 and Dye-3 after vs before they bound with soft-shelled turtle (*Trionyx sinensis*) liver RNA in PBS.

TABLE 2

| Dye | Relative fluorescence intensity | | Ratio of increase in fluorescence (after vs before binding) |
|---|---|---|---|
| | Before binding RNA | After binding RNA | |
| Dye-1 | 1.82 | 83.24 | 46 |
| Dye-2 | 0.97 | 37.28 | 38 |
| Dye-3 | 1.64 | 33.57 | 20 |

Example 14

Detection of the Fluorescence Intensity of Dye-0 in PBS Containing DNA

Figure 11:
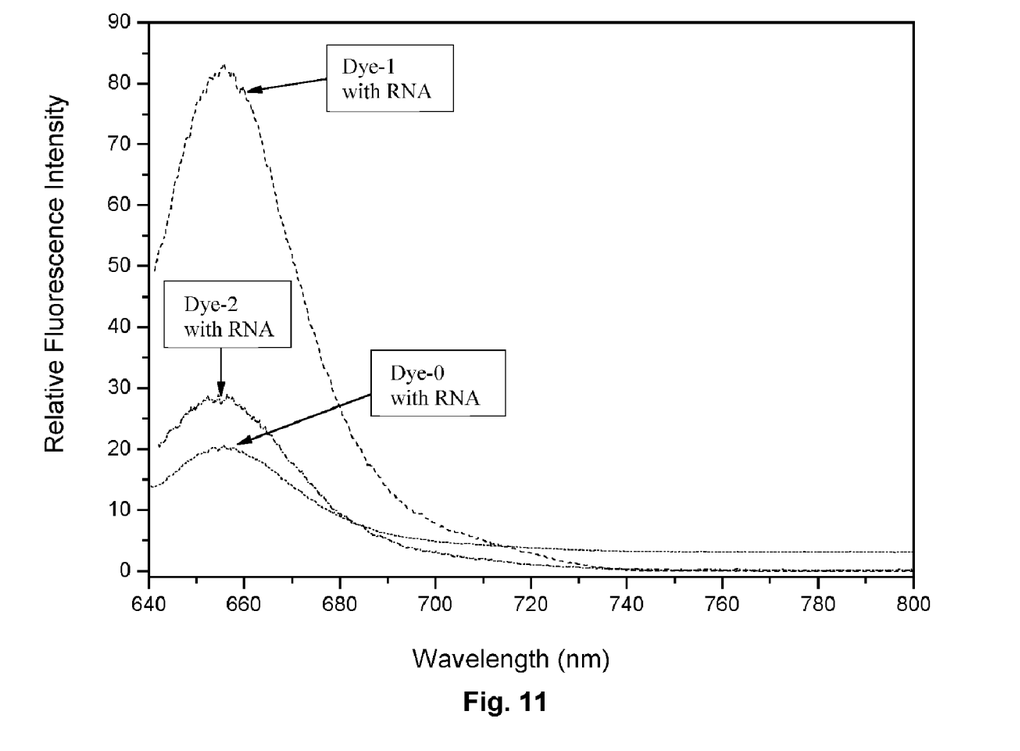
FIG. 11 is a comparison of the fluorescence emission spectra for Dye-0, Dye-1 and Dye-2 in PBS after they bind with soft-shelled turtle (*Trionyx sinensis*) liver RNA.

To illustrate how the compounds of the present disclosure improve the properties of fluorescent dyes, the known compound Dye-0 having the following structure is selected as the reference (Journal of the American Chemical Society (1945) 67, 18889-93):

The detection procedure followed was that described in Example 10. The fluorescence spectra for Dye-1, Dye-2 and Dye-0 after they bound in identical concentrations with soft-shelled turtle (*Trionyx sinensis*) liver RNA are shown in FIG. 11. As can be clearly seen from the figure, Dye-1 had the largest magnitude of increase in fluorescence intensity after it bound with RNA, and Dye-2 also showed marked increase in fluorescence intensity after it bound with RNA, an increase higher than that with Dye-0 that bound RNA, indicating that Dye-1 and Dye-2 are superior to Dye-0 in the ability to bind to nucleic acids.

Example 15

Detection of the Fluorescence Quantum Yields of Dye-1, Dye-2, Dye 3 and Dye-0 in Ethanol

Separate solutions of Dye-1, Dye-2, Dye-3 and Dye-0 in ethanol were prepared in concentrations that resulted in a maximum absorbance <0.1 on a UV-Vis spectrophotometer and were detected for their fluorescence intensities at selected excitation wavelengths. Each of the dyes were detected in triplicate at room temperature. Fluorescence quantum yields were calculated and averaged. With Rhodamine B as the standard ($\phi_F$=0.97, ethanol), the fluorescence quantum yield for the known compound M in the ethanol solution was calculated to be $\phi_F$=1.099×10$^{-2}$; for Dye-1, $\phi_F$=1.590×10$^{-2}$; for Dye-2, $\phi_F$=1.248×10$^{-2}$; and for Dye-3, $\phi_F$=1.181×10$^{-2}$. The instrument used was UV-Vis spectrophotometer Model Lambda 35, and fluorescence spectrophotometer Model FL-4500.

Data showed that the compounds of the present disclosure exhibited a higher fluorescence quantum yield than the known compound.

Although the present disclosure has been illustrated by way of the above embodiments and particular examples thereof, it will be appreciated by those skilled in the art that various changes, alterations and modifications may be made to the present disclosure without departing from the spirit and scope of the present invention as claimed.

The invention claimed is:

1. A compound having the structure of the following general formula I:

wherein
n is 1, 2 or 3;
X is $C(CH_3)_2$, O, S or Se;
$R_1$ and $R_2$ are each independently selected from at least one of the following: H, OH, $C_{1-18}$alkyl, $C_{1-6}$alkyl-$OR_5$, $C_{1-18}$alkylsulfo, phenyl and halogen;
$R_3$ and $R_4$ are each independently selected from at least one of the following: $C_{1-18}$alkyl-$COOR_6$ and benzyl, wherein said benzyl is optionally substituted with one or more substituents selected from at least one of the following: halogen, hydroxyl, sulfhydryl, cyano, nitro, alkyl, aryl, alkoxy, heterocyclyl, haloalkyl, amino, alkylamino, amido and carboxyl, provided that R3 and R4 are not simultaneously benzyl or simultaneously $C_{1-18}$alkyl$COOR_6$,
$R_5$ is $C_{1-18}$alkyl or H;
$R_6$ is $C_{1-18}$alkyl, H or phenyl, wherein said phenyl is optionally substituted with one or more substituents selected from at least one of the following: halogen, hydroxyl, sulfhydryl, cyano, nitro, alkyl, aryl, alkoxy, heterocyclyl, haloalkyl, amino, alkylamino, amido and carboxyl; and
$Y^-$ is an anion.

2. The compound according to claim 1, wherein $R_1$ and $R_2$ are both H.

3. The compound according to claim 1, wherein $R_3$ is $C_{1-6}$alkyl-$COOR_6$, or benzyl, wherein said benzyl is optionally substituted with one or more substituents selected from at least one of the following:
  halogen, hydroxyl, sulfhydryl, cyano, nitro, alkyl, aryl, alkoxy, heterocyclyl, haloalkyl, amino, alkylamino, amido and carboxyl.

4. The compound according to claim 1, wherein $R_4$ is $C_{1-6}$alkyl-$COOR_6$, or benzyl, wherein said benzyl is optionally substituted with one or more substituents selected from at least one of the following:
  halogen, hydroxyl, sulfhydryl, cyano, nitro, alkyl, aryl, alkoxy, heterocyclyl, haloalkyl, amino, alkylamino, amido and carboxyl.

5. The compound according to claim 1, wherein $R_5$ is H or $C_{1-6}$alkyl.

6. The compound according to claim 1, wherein $R_6$ is $C_{1-6}$alkyl or phenyl, wherein said phenyl is optionally substituted with one or more substituents selected from at least one of the following: halogen, hydroxyl, sulfhydryl, cyano, nitro, alkyl, aryl, alkoxy, heterocyclyl, haloalkyl, amino, alkylamino, amido and carboxyl.

7. The compound according to claim 1, wherein X is $C(CH_3)_2$ or S.

8. The compound according to claim 1, wherein n is 1 or 2.

9. The compound according to claim 1, wherein $Y^-$ is chosen from halogen ions, $ClO_4^-$, $PF_6^-$, $CF_3SO_3^-$, $BF_4^-$, acetate or p-toluenesulfonate anions.

10. A compound selected from:

-continued

-continued

11. A conjugate comprising the compound according to claim 1.

12. A composition for staining biological samples, wherein said composition comprises the compound according to claim 1 or a conjugate thereof.

13. The composition according to claim 12, wherein said biological samples are selected from nucleic acids, or leucocytes, erythroblasts, or reticulocytes in the blood.

14. A method of staining biological sample, comprising:
   obtaining a compound according to claim 1, or a conjugate or a composition including the compound; and
   staining the biological sample with said compound, conjugate or composition including the compound.

15. The method according to claim 14, wherein said biological samples are selected from at least one of: nucleic acids or leucocytes, erythroblasts, or reticulocytes in the blood.

* * * * *